US006801595B2

(12) United States Patent
Grodzins et al.

(10) Patent No.: US 6,801,595 B2
(45) Date of Patent: Oct. 5, 2004

(54) X-RAY FLUORESCENCE COMBINED WITH LASER INDUCED PHOTON SPECTROSCOPY

(75) Inventors: Lee Grodzins, Lexington, MA (US); Hal Grodzins, Bedford, MA (US)

(73) Assignee: Niton Corporation, Billerica, MA (US)

( * ) Notice: Subject to any disclaimer, the term of this patent is extended or adjusted under 35 U.S.C. 154(b) by 147 days.

(21) Appl. No.: 10/138,797

(22) Filed: May 3, 2002

(65) Prior Publication Data

US 2002/0168045 A1 Nov. 14, 2002

Related U.S. Application Data

(60) Provisional application No. 60/289,042, filed on May 4, 2001.

(51) Int. Cl.[7] ............................................ G01N 23/223
(52) U.S. Cl. ............................. 378/45; 356/72; 356/300
(58) Field of Search ............................. 378/45–49, 53; 356/72, 73, 300–330

(56) References Cited

U.S. PATENT DOCUMENTS 3,903,414 A * 9/1975 Herbstein et al. ............. 378/46
6,421,415 B1 * 7/2002 Peczkis et al. ................ 378/46
6,459,767 B1 * 10/2002 Boyer ........................ 378/121

FOREIGN PATENT DOCUMENTS

| JP | 08313460 | 11/1996 |
| JP | 09167789 | 6/1997 |
| JP | 09-167789 | * 6/1997 |

OTHER PUBLICATIONS

Freifeld, K., "Art Analysis: Probing Beneath the Image," *IEEE Spectrum*, IEEE Inc., Jun. 1, 1986, pp. 66–71, New York.

* cited by examiner

*Primary Examiner*—Craig E. Church
*Assistant Examiner*—Jurie Yun
(74) *Attorney, Agent, or Firm*—Bromberg & Sunstein LLP

(57) ABSTRACT

A device and method for identifying the composition of a target sample. The target sample may be a matrix such as a metal alloy, a soil sample, or a work of art. The device includes an x-ray fluorescence detector that produces an x-ray signal output in response to the target sample. The device also includes an optical spectroscope that produces an optical signal output in response to the target sample. Further, a processor is included that analyzes and combines the x-ray signal output and the optical signal output to determine the composition of the test material. In one embodiment, the optical spectroscope is a laser induced photon fluorescence detector.

14 Claims, 3 Drawing Sheets

X-RAY FLUORESCENCE COMBINED WITH LASER INDUCED PHOTON SPECTROSCOPY

CROSS REFERENCE TO RELATED APPLICATIONS

This application claims priority from U.S. Provisional Patent Application No. 60/289,042, filed May 4, 2001, having the title "X-Ray Fluorescence Combined with Laser Induced Photon Spectroscopy" which is incorporated by reference herein in its entirety.

TECHNICAL FIELD AND BACKGROUND ART

The present invention relates to devices for determining the composition of a test material and more specifically devices that use multiple fluorescence techniques for determining composition.

X-ray Fluorescence ("XRF") is one method for quantifying the elemental distribution of materials, but as the sought-for element gets lighter, XRF becomes less sensitive. As a general rule, XRF is useful for all elements heavier than about titanium. In special cases, XRF is effective for measuring the fractional weight of lighter elements; for example, sulphur in oil is easily quantified. However, the method ceases to have any quantitative value for carbon, oxygen, fluorine and sodium and other very light elements. To give a useful measure of these and other light elements, the preferred in situ method is optical spectroscopy.

Optical spectroscopy is a known technique for determining elemental and chemical compositions. Almost all portable optical spectroscopy systems currently available for measuring the elemental composition of alloys use a spark discharge to excite the optical spectrum to be analyzed. In recent years, lasers have been used to induce plasmas that result in fluorescent optical and near ultra-violet spectra. Variations of the basic technique involve different lasers and different spectrometers. The formed plasma may be of millimeter or micron size and the optical spectra may be viewed over microseconds or time-resolved in nanoseconds. The general technique is often referred to as laser-induced breakdown spectroscopy or LIBS, though sometimes it is referred to as laser-induced photon spectroscopy or LIPS.

New lasers and new modalities are regularly being developed so that the new acronym LIPF "laser induced photon fluorescence" is more appropriate. LIPF applies to any laser method for inducing photon spectra, from the infrared to the near ultra-violet, which results in the identification of the elements or compounds in any sample matrix.

In LIPF processes, molecules/atoms are excited to higher electronic energy states via laser absorption and subsequently fluoresce; the intensity of this fluorescence is, in general, a function of the species concentration (number density), and the gas temperature and pressure. Among other things, this fluorescence is linearly dependent on the absorber number density. By virtue of the fact that the energy states of molecules/atoms are quantized, the spectral absorption regions are discrete; however, for large molecules, the spacing of the discrete transitions may be sufficiently small (and the number of transitions sufficiently great) that discrete absorption regions are not observed (only absorption bands are observed). Typically, single-interaction fluorescence occurs at wavelengths greater than or equal to the laser wavelength, and again for atoms and diatomic molecules especially, discrete fluorescence transitions may be observed. LIPF while producing single-interaction fluorescence, more generally produces a high-temperature plasma in which atoms are excited to higher energies than the energy of the laser photons so that lower wave-length transitions are observed. For more information regarding LIPF see Romero et al.,"Surface and tomographic distribution of carbon impurities in photonic-grade silicon using laser-induced breakdown spectrometry" Journal of Analytical Atomic Spectrometry, Vol. 13, June 1998 which is incorporated herein by reference in its entirety. See also Hwang, "A feasibility study of micro-laser induced breakdown spectroscopy applied to lead identification in metal alloys and environmental matrices" Thesis (S.M.) Massachusetts Institute of Technology, indexed (OcolC)48198136 (1998) which is attached hereto as appendix A and is incorporated by reference herein in its entirety.

LIPF has the potential to measure the distribution of almost all elements in any matrix. In practice, the method has commercial sensitivity for a subset of elements, though with the proper choice of laser, that subset can encompass the most important light elements in a given application. LIPF, however, has the general drawback that the efficiency of production of the optical emissions, that is, the intensities of the induced spectral lines, depends strongly on the matrix and the measuring conditions. Comparison standards are essential.

Although both LIPF and XRF are known techniques, the techniques have not been combined into a single device to produce a more complete composition of a test material. Further, the measurements have not been graphically combined and scaled to provide a spectral representation on a graphical display device.

SUMMARY OF THE INVENTION

In a first embodiment of the invention there is provided a device for identifying the composition of a target sample. The target sample may be a matrix such as a metal alloy, a soil sample, or a work of art. The device includes an x-ray fluorescence detector that produces an x-ray signal output in response to the target sample. The x-ray fluorescence detector is sensitive to elements above a particular threshold. In general the threshold element is titanium. The device also includes an optical spectroscope that produces an optical signal output in response to the target sample. In one embodiment, the optical spectroscope is a laser induced photon fluorescence detector. The laser induced photon detector is sensitive to the lighter elements below the threshold that typically include sodium, carbon and oxygen. Further, a processor is included that analyzes and combines the x-ray signal output and the optical signal output to determine the composition of the test material. The processor receives the output signals from the x-ray fluorescence detector and the laser induced photon detector and begins to analyze the data. The analysis determines the type of material that is being processed, such as, a metal alloy that is an aluminum alloy. The processor then compares the data from the output signals concerning the common element and then scales the optical signal output data to produce a displayable output that contains the concentrations of elements within the test material. In one embodiment, the x-ray fluorescence detector, the optical spectroscope and the processor are contained within a single housing. In other embodiments, the x-ray fluorescence detector and the optical spectroscope are not in the same housing, yet share a common processor.

In general, the data that is contained within the optical signal output is relative data concerning the concentrations of elements in the test sample, while the data that is contained within the x-ray signal output is absolute. To produce an output signal which can be displayed and which provides data regarding the concentration of elements in the test material, both the laser induced photon fluorescence detector and the x-ray fluorescence detector are sensitive to at least one common element within the target sample. The processor uses data from the optical signal output and the x-ray signal output about the common element to normalize data contained within the optical signal output.

In another embodiment, the laser induced photon detector and the x-ray fluorescence detector are positioned within the device so that both analyze a common area of the target sample. The two detectors within the device may operate simultaneously in one embodiment to produce their respective output signals that are transferred to the processor. In another embodiment, the x-ray fluorescence detector operates first. In the preferred embodiment, the length of time that it takes to measure the test material is shorter than the time for removal of the test material from the device and insertion of the test material in a second device for analysis. Further, the device can be sized to be both portable and battery operated.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
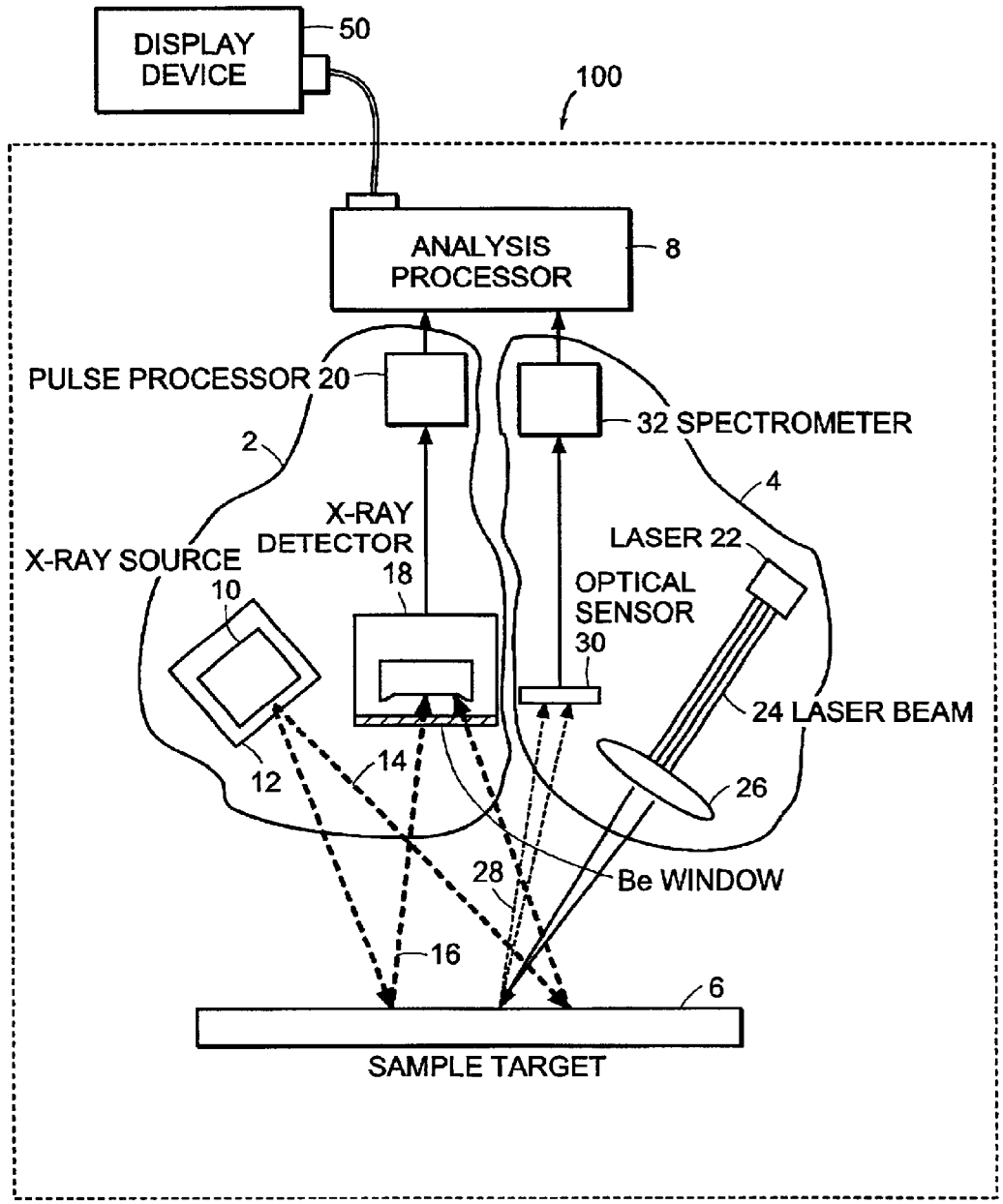
FIG. 1 is a device for determining the composition of a test material such as a metal alloy, soil, artwork or any matrix.

FIG. 1 is a device 100 for determining the composition of a test material such as a metal alloy, soil, artwork or any matrix. The device incorporates both an XRF detector 2 along with a LIPF (Laser Inducted Photon Fluorescence) detector 4. The two detectors are electrically coupled to an analysis processor 8. The analysis processor 8 receives measurement signals from the XRF detector 2 and the LIPF detector 4 and analyzes the produced data to determine the elements which are the composition of the test material. The LWPF 4 detector may use either continuous or time-resolved spectroscopy. In one embodiment, the measurements made by the XRF and LIPF detectors occur within seconds of each other. In other embodiments, the measurements occur simultaneously. Preferably, the detectors work in conjunction such that the measurements take place during an interval which is less than the time it would take to remove the test sample from an XRF detector and place the test sample in a separate LIPF detector. In certain embodiments, the XRF detector and the LIPF detector are contained within a common housing. In other embodiments, the laser of the LIPF detector may be separated from the XRF detector, but still shares a common analysis processor and display device.

During the testing by the device 100, the volume of the sample being measured by XRF overlaps with the volume of the sample being measured by LIPF technique; and the information from the XRF and LIPF detectors 2, 4 are analyzed together. The measurements are made consistent by complementary information which is used to normalize the results such that a single graphical display may identify the elemental distributions that compose the target sample. Coupled to the processor in various embodiments is memory which provides for the storage and future retrieval of the data which represents the composition of the test material.

The XRF detector 2 and the LIPF detector 4 view a common target area 6; the area struck by the x-ray beam 14 overlaps the much smaller area struck by the laser beam 24. The analysis processor 8 are also common to both the XRF and LLPF units 2, 4. Although in other embodiments, separate processors may be provided for both the XRF detector 2 and the LIPF detector 4 if the detectors operate simultaneously.

The XRF unit 2 includes an x-ray or gamma ray source 10, which may be a radioactive source or an x-ray tube. The emitted radiations 14 strike the sample 6 inducing fluorescent radiation 16 that are detected in the suitable detector 18. The detected events are processed in the pulse processor 20, and the results of the distribution of pulse strengths sent to the analysis processor 8.

The LIPF unit 4 includes a laser 22 whose beam 24 is focused by a lens system 26 onto the target 6. Lasers such as "Frequency-Quadrupled Microchip Laser", invented by John Zayhowski of Lincoln Labs is preferably used. It includes a Nd:YAG laser whose primary frequency is quadrupled to produce an excitation frequency of 266 nm that can be used for creating a plasma that results in the 194 nm fluorescence line for carbon. It should be understood by one of ordinary skill in the art that other lasers may be used which are capable of producing fluorescence lines for desired elements.

The fluoresced spectrum 28 is captured into the spectrometer 32 by a lens system 30. The spectrometer results are then transmitted to the analysis processor 8. The results of the analysis of the XRF data and the LIPF data are combined in analysis processor 8 and displayed on a single screen 50. The display screen may be an integral part of the device or may be a separate component.

The output from the optical spectrometer 32 can be in many forms. For example, the output may be the intensities in each of the pixels of a CCD camera that is at the focal plane of the spectrometer. That output, which gives the spectral information in the form of positional intensities in the CCD is read by the processor and analyzed to correct for interferences; the processor determines the relative strengths of elements on the basis of the relative strengths of signature lines. In another embodiment, the output of the LIPF detector is the result of a series of individual detectors such as PIN silicon diodes or silicon avalanche diodes, wherein each detector is position sensitive to a particular signature wave length or a neighboring line to serve as normalization. The analysis processor then analyzes the results as a function of diffraction position, strength of signal, and the time that the signal was detected, referenced to the laser pulse. The results of the two measurements are then integrated in the processor which scales the LIPF measurements, which are generally relative, with the absolute values obtained by XRF as explained below with respect to the flow chart of FIG. 2.

Figure 2:
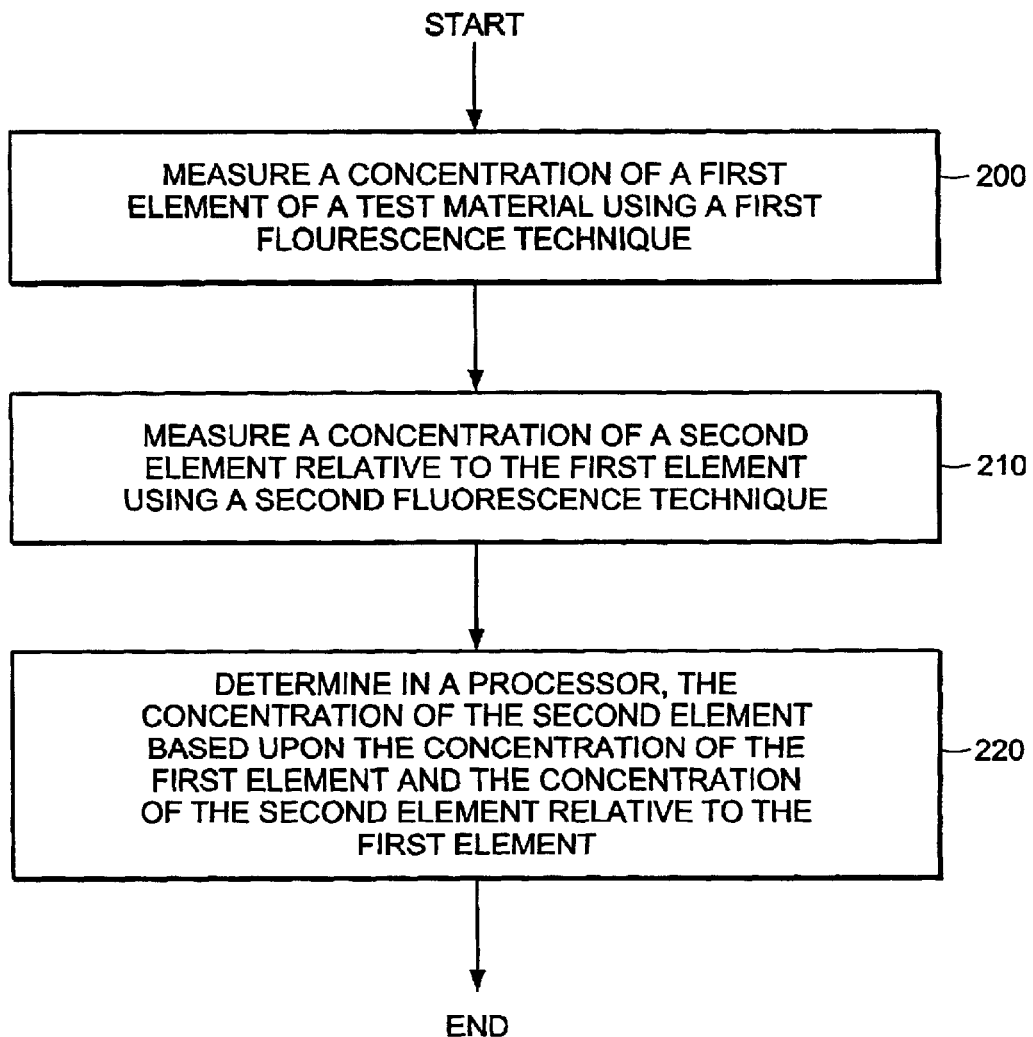
FIG. 2 is a flow chart of the steps for producing a coherent output which may be displayed on a display device showing the spectral make-up of a test material.

FIG. 2 is a flow chart which shows the steps for producing a coherent output that may be displayed on a display device showing the spectral make-up of a test material. First, an element which is part of the target sample and which can be identified by two fluorescence techniques (for example XRF and LIPS) is measured using a first fluorescence technique such as XRF (Step 200). For example, for a carbon steel target sample, iron would be measured first by the XRF detector. From the measurement, a concentration is determined within the analysis processor. The concentration provides an absolute measurement of the quantity of the first material. For example, iron might be measured and 60% concentration of iron might be found in the test sample. A measurement is then taken using a second fluorescence technique, such as LIPF, where relative concentrations of elements of the target sample are determined (Step 210). The relative concentrations are for at least the element that can be determined by the first fluorescence technique and another element. For example, carbon, which is the second element, may be 1% of the iron content which is the first element that is deterrmined absolutely by the first fluorescence technique. The absolute concentration of the second element is determined from the absolute concentration of the first and the relative information regarding the first and second elements (Step 220). For example, if iron was 60% of a steel alloy and carbon was 1% of the iron concentration then carbon would be 0.6% of the test sample. This is repeated for each of the elements which are identified using the second fluorescence technique. For example, absolute concentration measurements for lighter elements such as oxygen would be determined using the absolute concentration information concerning the overlapping element, which in this example is iron and the relative information between iron and oxygen.

Figure 3:
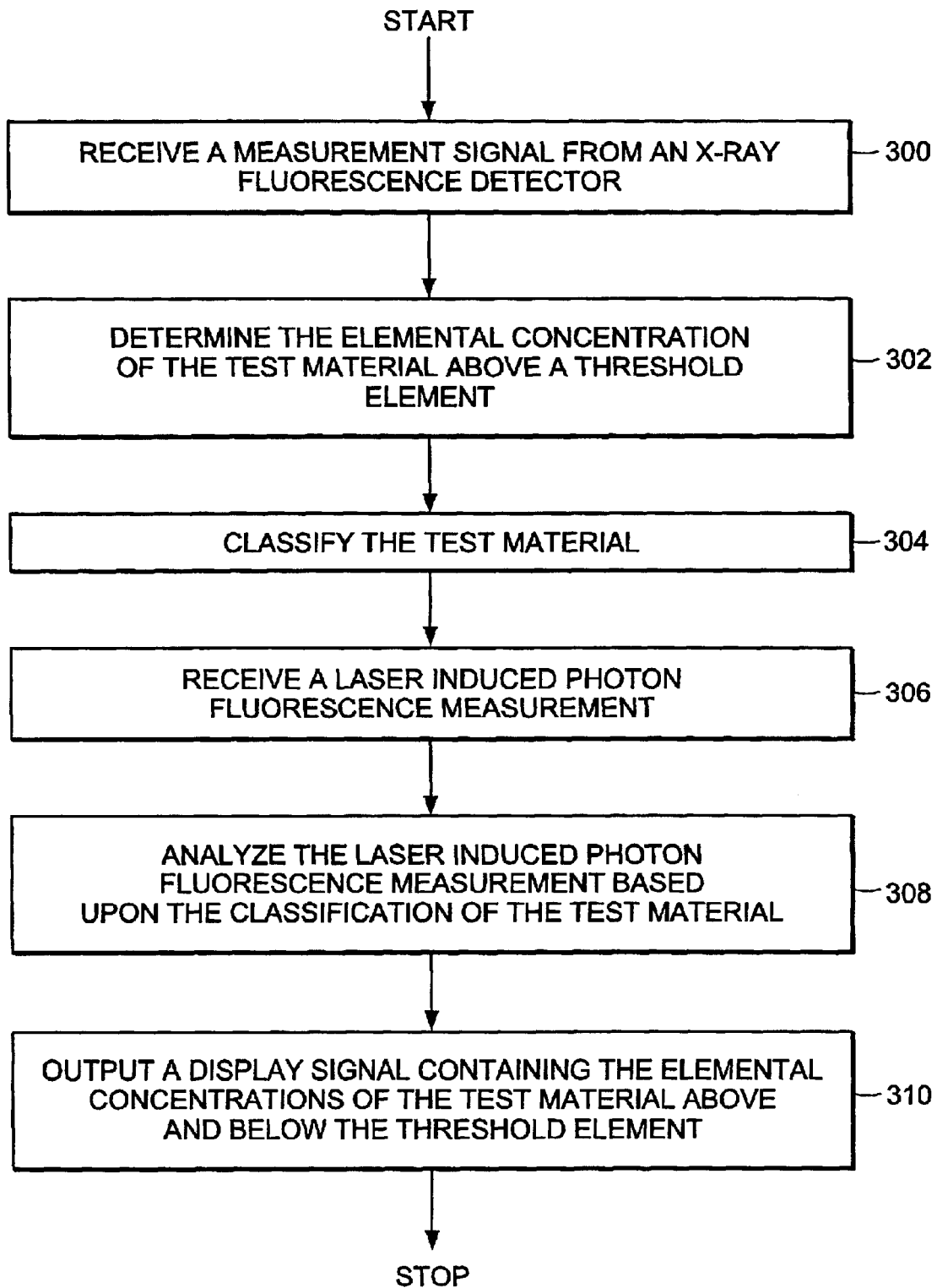
FIG. 3 is a flow chart providing the steps used to produce a display signal by the analysis processor.

FIG. 3 is a flow chart which provides the steps used to produce a display signal by the analysis processor. In this embodiment, the XRF measurements are performed first. The X-Ray detector passes the measurement signal to the pulse processor, which amplifies and filters the measurement signal which is then passed to the analysis processor which receives the signal. (Step 300). The analysis processor analyzes the signal from the pulse processor determining the elemental concentration of the heavier elements (in general, those above titanium) (Step 302). Based on this information, the test sample is classified (Step 304). For example, if the analysis processor identifies the material as iron with at most 0.5% light element concentration, the analysis processor accesses a look-up table in associated memory and identifies the material as carbon steel. This classification is then stored in memory. The LIPF detector is then made active by the analysis processor. The laser is turned on and the laser measurement signal of the fluoresced target sample is passed from the spectrometer to the analysis processor (Step 306). The analysis processor uses the stored alloy classification to process the LIPF measurement signal from the spectrometer (Step 308). For example, the XRF measurement signal identifies the material as one of a small class of alloys that contain, for example, 95% light elements and therefore is an aluminum alloy. The analysis processor then analyzes the LIPF measurement signal to get the aluminum, sulfur, etc elements, iterating the analysis of the results to make a consistent final analysis. In another example, if the material is classified by the analysis processor as carbon steel, the analysis processor then analyzes the LIPF measurement signal to determine the carbon concentration. Once all of the elements that compose a test sample are determined along with each element's absolute concentration, this information is provided in the form of a display signal (Step 310). The display signal can be forwarded to a display device such that a more complete spectral composition can be shown as compared to that of a single fluorescence technique measurement device.

Combining LIPF and XRF measurements on the same sample volume of a target sample has important advantages. The complementary data results in a greater number of elements being measured; for example, LIPF may yield the carbon concentration in a steel alloy as explained above, while XRF yields the concentration of all the heavy metals in that alloy. Overlapping data regarding the same element of a target sample gives the combined technique an advantage since in most applications, such as the inspection of alloys, LIPF can measure the intensity of the spectral lines from at least one of the heavy elements that XRF can measure absolutely. In that case, the XRF result can be used to normalize the LIPF results so that all of the relative measurements made by LIPF can be made absolute. The single, integrated unit will be considerably less costly than the sum of the costs of separate units as a result of savings in analytic firmware and in the hardware of packaging. Results of the combined analytic measurements will be obtained immediately without the time-consuming need for combining the results off-line.

The device as disclosed may be a stationary instrument such as bench-top unit or a transportable, portable, hand-held, instrument. The preferred embodiment is a battery-operated hand-held instrument.

In an alternative embodiment, the methodology performed within the analytic processor may be implemented as a computer program product for use with a computer system including digitization devices. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A device for identifying the elemental composition of a target sample, the device comprising:

an x-ray fluorescence detector producing an x-ray signal output in response to the target sample emitting fluoresced x-rays upon being exposed to a radiation source;

an optical spectroscope producing an optical signal output in response to the target sample emitting an optical emission upon being exposed to a plasma creating laser; and a processor for analyzing the x-ray signal output and the optical signal output to determine the elements of the target sample, based in part on relative-concentration of elements determined from the optical signal based in part on relative concentration of elements determined from the optical signal.

2. The device according to claim 1, wherein the optical spectroscope is a laser induced photon fluorescence detector.

3. The device according to claims 2 wherein both the laser induced photon-fluorescence detector and the x-ray fluorescence detector are sensitive to at least one common element.

4. The device according to claim 3, wherein the processor uses data from the optical signal output and the x-ray signal output about the common element to normalize data contained within the optical signal output.

5. The device according to claim 2, wherein the laser induced photon detector and the x-ray fluorescence detector are positioned within the device so that both analyze a common area of the target sample.

6. The device according to claim 2, wherein the laser induced photon fluorescence detector and the x-ray fluorescence detector are coupled to the processor wherein the processor is configured to operate the detectors substantially simultaneously.

7. The device according to claim 1, wherein the processor outputs a signal of the composition of the test material capable of being displayed on a display device.

8. The device according to claim 1, wherein the device is a portable device.

9. The device according to claim 8, wherein the device is battery operated.

10. The device according to claim 1, wherein the x-ray fluorescence detector is capable of identifying elements in the test material which are heavier than titanium.

11. The device according to claim 1, further comprising:

a housing which contains both the x-ray fluorescence detector and the optical spectroscope.

12. A method for determining the elemental composition of a test material, the method comprising:

measuring a concentration of a first element of the test material using x-ray fluorescence analysis;

measuring a concentration of a second element relative to the first element using laser induced photon spectroscopy analysis;

determining in a processor the concentration of the second element based upon the concentration of the first element and the concentration of the second element relative to the first element.

13. A method according to claim 12, wherein the x-ray fluorescence cannot measure the concentration of the second element.

14. The method according to claim 12, wherein the second element has an atomic weight which is less than the first element.

* * * * *

UNITED STATES PATENT AND TRADEMARK OFFICE
CERTIFICATE OF CORRECTION

PATENT NO. : 6,801,595 B2
APPLICATION NO. : 10/138797
DATED : October 5, 2004
INVENTOR(S) : Lee Grodzins et al.

Page 1 of 1

It is certified that error appears in the above-identified patent and that said Letters Patent is hereby corrected as shown below:

In Col. 7, lines 14-16 delete "based in part on relative concentration of elements determined from the optical signal"

Signed and Sealed this

Twenty-fifth Day of December, 2007

JON W. DUDAS
*Director of the United States Patent and Trademark Office*